United States Patent
Pigg et al.

[11] Patent Number: 6,142,968
[45] Date of Patent: Nov. 7, 2000

[54] FABRIC ARTICLE WITH EXTENSION INDICATOR

[75] Inventors: William Pigg, Elvington; Joseph William Robinson, Over, both of United Kingdom

[73] Assignee: Smith & Nephew Plc, United Kingdom

[21] Appl. No.: 08/930,348

[22] PCT Filed: Apr. 1, 1996

[86] PCT No.: PCT/GB96/00774

§ 371 Date: Nov. 12, 1997

§ 102(e) Date: Nov. 12, 1997

[87] PCT Pub. No.: WO96/31175

PCT Pub. Date: Oct. 10, 1996

[30] Foreign Application Priority Data

Apr. 1, 1995 [GB] United Kingdom .................. 9506804
Jun. 6, 1995 [GB] United Kingdom .................. 9511397

[51] Int. Cl.[7] ..................................... A61F 13/00
[52] U.S. Cl. .................................. 602/75; 602/76
[58] Field of Search ................. 602/75, 76, 77, 602/78; 28/155, 172.2, 184, 194, 213

[56] References Cited

U.S. PATENT DOCUMENTS 3,613,679  10/1971  Bijou ........................................ 602/75

FOREIGN PATENT DOCUMENTS 9412133  6/1994  WIPO ...................................... 602/75

Primary Examiner—Kim M. Lee
Attorney, Agent, or Firm—Larson & Taylor, PLC

[57] ABSTRACT

There is disclosed an extensible article comprising an extensible fabric and an indicator for showing when the fabric has reached a predetermined degree of extension, a method for forming such articles and a method of treatment of venous disorders comprising applying said article to an affected site on a patient.

17 Claims, 2 Drawing Sheets

FABRIC ARTICLE WITH EXTENSION INDICATOR

This application is a 371 of PCT/GB96/0074 filed Apr. 1, 1996.

BACKGROUND OF THE INVENTION

The present invention relates to extensible articles, methods for making such articles and to methods of assessing the degree of extension of such articles.

For many extensible articles it is desirable to be able to assess when a pre-determined degree of extension has been achieved. For example it may be desirable to know when a particular material has been extended to a value which is close to its elastic limit in order to avoid exceeding said limit.

In the field of medicine, extensible fabrics are often used in dressings and bandages and if these are applied too tightly to a patient problems may result due to the high pressure applied. In extreme cases blood flow can be severely impaired and damage to body tissues can result.

This is a problem which is well known and which has existed for many years in the field of bandages.

Woven or knitted elastic bandages in both adhesive and nonadhesive forms are used to provide support, to assist in the healing of strained muscles and in the treatment of various venous conditions. Conventional elasticated woven or knitted bandages have one or more warp yarns which comprise elastomeric materials such as natural rubber or synthetic elastomeric materials such as polyurethane. It is important that these bandages are applied at a tension which is sufficiently high to enable them to maintain an effective level of compressive force under the bandage over a period of time.

U.S. Pat. No. 4,653,492 discloses an elastic bandage having a resilient elastic layer and a relatively non-resilient elastic layer to limit the stretching of the elastic layer so the bandage is not applied too tightly.

U.S. Pat. No. 4,366,814 discloses an elastic bandage material comprising at least 50 percent by weight of an extensible fabric capable of elongation of at least 30 percent without tearing and at least 15 percent of an elastomer impregnated in a fabric. The bandage material is said to be especially suited for use as a backing for adhesive tapes and dressings.

Patent application no FR-A-2,542,201 discloses a surgical support which is said to be extensible in all directions and impermeable to liquids, characterized in that it comprises a polyurethane film and a non-woven elastomeric material which is stretchable in all directions and which penetrates through the thickness of the polyurethane film, the fibers of the non-woven material each having a length greater or equal to 6 cm. The surgical support is of use in the field of wound dressings. It is prepared by depositing a polyurethane containing liquid composition on a temporary support, introducing in situ the non-woven material. and then drying.

However, a disadvantage associated with the known woven or knitted bandages discussed above is that if they are stretched too much during the application, the compression force under the bandage may be too much and cause damage, for example by restriction of the blood supply.

In order to alleviate these problems it is known to mark bandages with markings which adopt a particular identifiable configuration when a bandage has been stretched to a certain degree. Such bandages are disclosed in U.S. Pat. No. 3,613,679, Patent application nos EP 0,475,811, DE 3,640,979 and DE 2,329,371. Thus when the particular configuration is achieved, a person applying the bandage may determine visually that a desired degree of extension has been achieved. For example. it is known to provide compression bandages having markings which appear as squares when a planar bandage is stretched to a desired degree and which in an unstretched state appear as narrow rectangles.

However, these bandages suffer from the disadvantage that it is often difficult to assess when a desired degree of extension has been achieved.

This is because bandages are applied by different users in different manners and therefore there is considerable variation between users in the degree of overlap of layers of bandage, the angle at which the bandage is applied relative to a longitudinal axis along a body member, etc. Furthermore limbs are irregular in shape and vary considerably from patient to patient.

Patent Application No. WO94/12133 discloses a bandage with a geometrical image knitted into the bandage where the image configuration changes on stretching.

Patent application no DE 2,329,371 additionally discloses a bandage with a creased indicator glued onto the bandage which extension on the bandage unfolds.

However the preparation of such a bandage requires a lengthy process incorporating a number of steps. Additionally such bandages are not as soft and easy to apply.

There is thus a need to provide an effective, convenient and inexpensive way of determining when an extensible article (e.g. an elastic bandage) has been extended to a particular degree.

SUMMARY OF THE INVENTION

According to the present invention there is provided an extensible article comprising an extensible fabric and an extension indicator, wherein said indicator is interlaced with said extensible fabric.

The extensible fabric may be any appropriate knitted, woven or non-woven material. Preferably the fabric is woven.

The extensible fabric may be elastic. Suitably the fabric comprises elastic fibers. The term fiber when used herein includes threads, filaments and yarns.

Preferably the indicator is a flexible elongate member, most preferably with a length at least ten times its width, and desirably it is located above a surface of the fabric in order that it can be easily viewed. Suitably said indicator comprises a plurality of loops.

Said indicator provides a means for assessing tension in an extended article, where the desired degree of tension can be pre-determined.

There is provided an extensible article wherein said indicator is interlaced with said article at least first and second points which become increasingly separated as the fabric is extended.

The term interlaced includes any suitable means for interlinking the indicator with the extensible article for example by weaving, knitting, stitching or sewing.

Further there is provided an extensible article wherein said loop adopts a configuration on extension of the fabric to the pre-determined extent which is visually distinct from the configuration adopted when the fabric is below the pre-determined degree of extension.

The indicator may adopt a linear configuration when the extensible fabric has been stretched to the pre-determined extent since at this degree of stretch of the fabric the indication may just become taut, whereas at lower degrees of stretch the indicator may be slack and adopt a relatively irregular configuration. By constraining the elongate member between the first and second attachment points using constraining means it can be caused to adopt other configurations when taut.

In another embodiment of the present invention there is provided a further indicator means comprising a fiber which may be threaded through indicator loops which are formed from or attached to the fabric in a desired arrangement (e.g. in a zig-zag arrangement).

Preferably said further indicator is substantially continuous in the direction of extension.

It should be noted that the elongate member need not be in a relatively slack state prior to the pre-determined degree of extension of the extensible fabric being achieved since it may be held under a degree of tension by releasable securing means (e.g. adhesive, stitching, tape etc.) which causes the elongate member to adopt a particular initial configuration when the extensible fabric has not been stretched to the pre-determined degree. Only when the pre-determined degree of extension has been achieved, is the elongate member released from the releasable securing means so that the initial configuration is destroyed.

Desirably the indicator does not substantially impede stretching of the extensible fabric i.e. the force required to stretch the fabric to a given degree is not substantially increased by the presence of the indicator.

The indicator may itself be elastic or inelastic. In the former case once the said pre-determined degree of extension has been achieved the indicator may be elastically extendible until a further degree of extension of the fabric is achieved, at which point the indicator breaks since it has reached its breaking strain. In this case the breaking strain of the indicator is preferably substantially below that of the extensible fabric.

By choosing an appropriate indicator, a target range of extensions of the fabric can be that selected to be the range between the said pre-determined degree of extension and the said further degree of extension. This range can therefore be assayed using a single indicator.

An alternative way of determining when the fabric is within a desired range of extension is to provide it with two or more indicators, each of which undergoes a change in configuration at different degrees of extension of the fabric.

This is not the only reason for providing a plurality of indicators, however, since one or more indicators may be placed at different positions which are spaced from one another along a direction of extension of the fabric in order to assess extension at different regions of the fabric. Here the indicators may indicate the same degree of extension if it is desired for the fabric to be stretched to the same degree along its length or they may indicate different degrees of extension if it is desired for the fabric to be stretched to different degrees along its length to provide enhanced graduated compression.

The indicator preferably contrasts in colour and/or design with the elastic fabric in order that it can be clearly seen.

The indicator may be located centrally or along an edge of the article. If more than one indicator is provided these may be located together or separately to enhance visibility on application of the article, for example in bandage form, to a patient.

A preferred indicator is a fiber an assembly comprising a plurality of fibers.

The indicator is aptly at least 0.1 cm long, and may be at least 5 cm long (when measured along the length of the indicator prior to stretching of the fabric). Stretching of the fabric to the pre-determined extent may cause the spacing between the first and second attachment points to increase by at least 10, 50, 100 or 200% for example.

Said further indicator as herein before described may suitably be the length of the fabric.

The extensible article may be in the form of a woven fabric. Elastication may be achieved by using twisted yarns bulked yarns or elastomeric yarns. Woven fabrics may have any of the weaving patterns which are conventionally used for making elastic bandages. The woven fabric comprises warp and weft threads. The elastic yarn can be present in the warp wherein a proportion of the warp threads are elastic yarn. Thus depending upon the weight of elastomeric polymer required in the article every 2nd, 3rd, 4th, 5th etc., warp thread may be an elastic yarn. Suitably the elastic yarn is woven into the fabric under tension and the woven material is allowed to relax. When in use the article is re-extended and applied to the affected part it provides the required compressive force.

The indicator is incorporated as part of the weaving process by altering the frequency of weft insertion wherein the yarn is threaded through separate shafts which can lift said yarn to a different lifting plane to the ground yarns. This allows the yarn to float over the ground yarns, which on relaxation of the article form clearly visible loops. Any number of such warp threads may be used to form indicators. There may be at least one such thread, preferably at least two, off centre, on the same or opposite side of the article to prevent overlapping on application of the article obscuring said indicator.

By altering the tension under which the article is being woven and therefore the length of the indicator, the indicator may be used to aid application of said article at different, predetermined extensions along the length of said article.

The article may be an article of clothing, or a medical dressing such as a bandage or a wound dressing. Preferably the article is a compression bandage. Typically bandages are in the form of elongate strips which may be of very large length but of relatively narrow width (which is usually constant). The width is usually less than 30 cm and is generally less than 20 cm.

The bandage may be provided with one or more markings to assist medical staff in overlapping layers of bandage to a given degree. Such markings are well known in the art and are typically in the form of one or more colored threads which extend along the length of the bandage and which form part of the elastic fabric of the bandage.

The bandage may be provided in sterile form and in a sealed package.

According to a further feature of the invention there is provided a method of treatment of one or more of the following disorders; namely venous disorders, lymphodoema, which comprises applying a bandage or article according to the invention to the affected site on a patient.

The present invention also provides a method for forming an extensible article according to the present invention, comprising preparing an extensible fabric stretched to a pre-determined extent and interlacing an indicator with the fabric to adopt a configuration which is visually distinct from the configuration adopted when the fabric is below the pre-determined degree of extension.

The present invention also provides a further method for forming an article of the present invention, comprising weaving fabric under tension and altering the frequency of weft insertion at predetermined points, wherein the indicator is interlaced as part of the weaving process as hereinbefore described.

Further said extensible article may be formed by preparing a fabric under tension and interlacing the indicator by stitching in indicator loops. The stitching may occur simultaneously in the process of preparing the bandage.

Said loops may alternate on both sides of the material.

A further indicator may be interlaced by threading a fiber through smaller loops. Said loops may be at least 0.1 cm long and may be formed for example in a linear or zig-zag arrangement.

The present invention will now be described by way of example only with reference to the accompanying drawings; wherein

The views shown are schematic and are not drawn to scale.

DETAILED DESCRIPTION OF THE INVENTION

Figure 1:
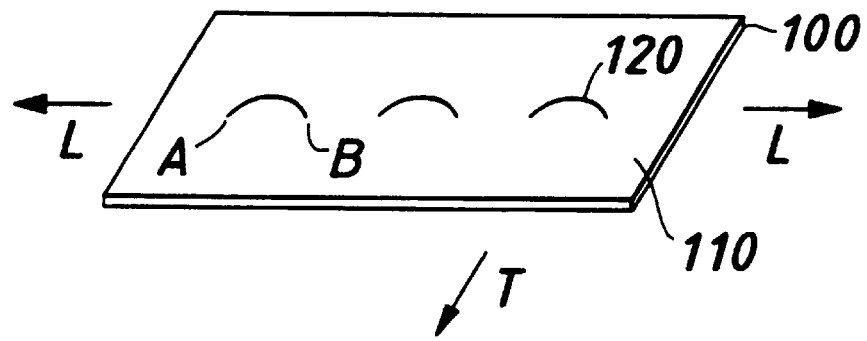
FIG. 1 shows a plan view of a section of an article according to the present invention in the form of a woven bandage which is shown in inextended form.

Referring now to FIG. 1, a section of woven compression bandage 100 is shown formed of a substrate 110 which has elastomeric fibers along the longitudinal direction (indicated by arrows "L") and which has substantially inextendible fibers along the transverse direction (indicated by arrow "T").

Thus the bandage 100 is extendible longitudinally but not transversely. In the drawing the bandage 100 is shown laid flat in an inextended state.

In order to assist in determining when 50% longitudinal extension of the bandage 100 has been attained, loops 120 are provided. At points A and B on the bandage 100, which lie along a line defining the direction of longitudinal extension of the bandage 100, loops 120 are held in fixed relation to substrate 110 by being interlaced into substrate 110. The length of loop 120 measured along the loop 120 between points A and B is 50% greater than the distance between points A and B when measured along upper surface 120 of inextended substrate 110.

Figure 2:
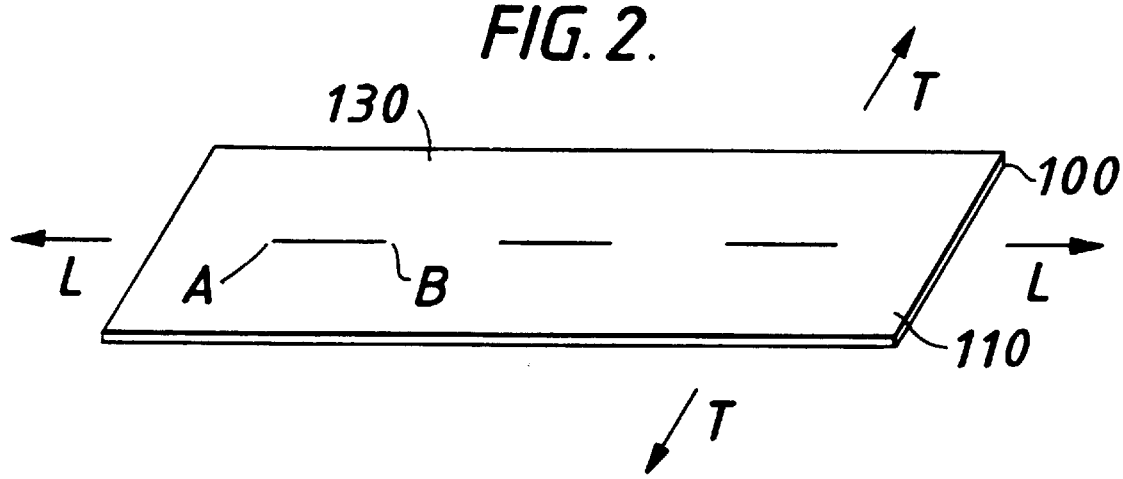
FIG. 2 shows a plan view of the section of bandage illustrated in FIG. 1 in extended form.

Turning now to FIG. 2, the section of bandage 100, shown in FIG. 1 is shown in a state in which it is extended longitudinally by 50%. Loop 120 now is taut and flat against upper surface 130 of substrate 110 and forms a straight line configuration between points A and B. This can be easily seen by a person applying the bandage since loop 120 is colored to contrast against substrate 110.

Loop 120 may be formed of relatively inextendable material which breaks at tensions just above the tension in which the pre-determined degree of stretching of the fabric is attained (e.g. thin cotton thread). Alternatively it may be an elastic material which is capable of a limited degree of further extension and which thus indicates a range of extensions of the bandage.

Figure 3:
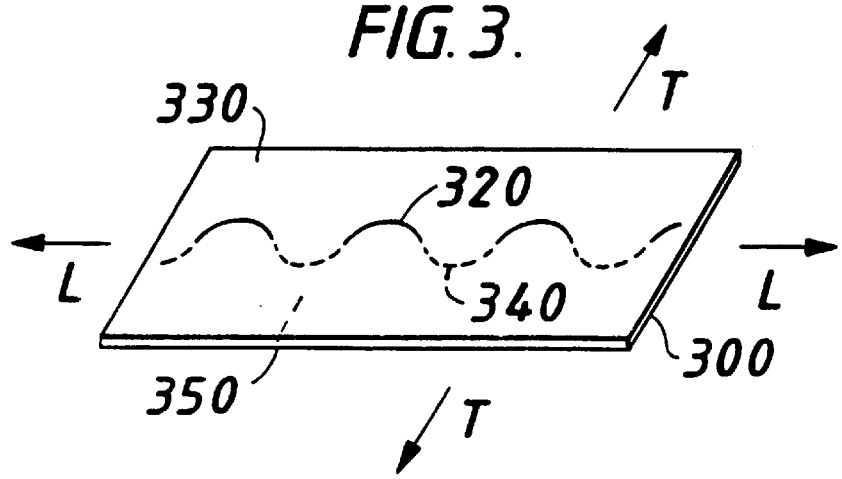
FIG. 3 shows a plan view of an alternative bandage according to the present invention in inextended form.

Referring to FIG. 3, a section of bandage 300 is shown, which is similar to that shown in FIG. 1, except that loops 120 are interlaced with substrate 110 by a stitching process forming loops 320 and loops 340 on opposite sides of the substrate (330, 350)

Figure 4:
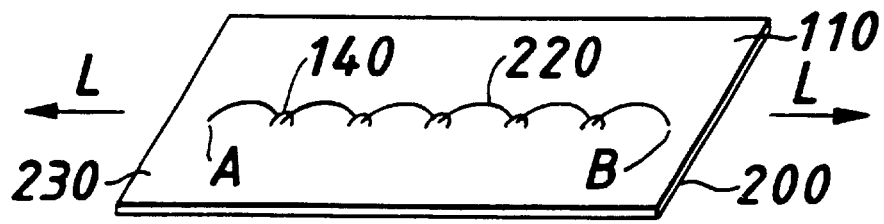
FIG. 4 shows a plan view of a section of another bandage according to the present invention which is shown in inextended form.
Figure 4:

Referring now to FIG. 4, a section of woven compression bandage 200 is shown formed of a substrate 110 which has elastomeric fibers along the longitudinal direction (indicated by arrows "L") and which has substantially inextendible fibers along the transverse direction (indicated by arrow "T").

Thus the bandage 200 is extendible longitudinally but not transversely, In the drawing the bandage 200 is shown laid flat in an inextended state.

In order to assist in determining when the required longitudinal extension of the bandage 200 has been attained, a further indicator, thread 220 is interlaced through loops 140. At points A and B on the bandage 200, which lie along a line defining the direction of longitudinal extension of the bandage 200, thread 220 is held in fixed relation to substrate 110.

Loops 140 are sewn into substrate 110 and are in a spaced linear relationship to one another. They are sufficiently large so that thread 220 is able to slide through them along the longitudinal direction in a substantially unimpeded manner.

Loops 140 aid in keeping thread 220 in close proximity to substrate 110 and thus aid in avoiding snagging as might occur if thread 220 were not constrained between points A and B.

Figure 5:
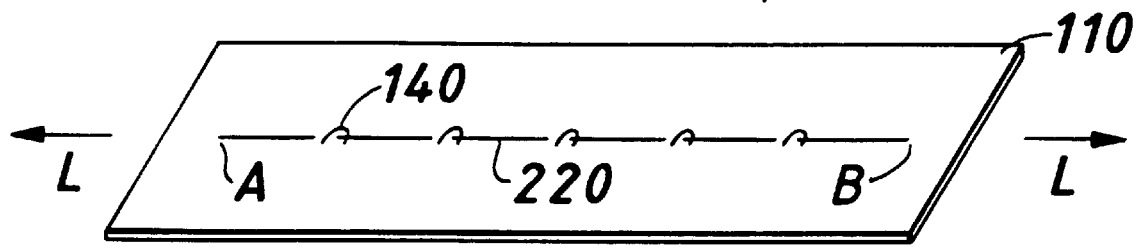
FIG. 5 shows a plan view of the section of bandage illustrated in FIG. 4 in extended form.
Figure 5:

Turning now to FIG. 5, the section of bandage 200, shown in the FIG. 4 is shown in a state in which it is extended longitudinally by the required amount. Thread 220 now is taut and flat against upper surface 230 of substrate 110 and forms a straight line configuration between points A and B. This can be easily seen by a person applying the bandage since thread 220 is colored to contrast against substrate 110.

Thread 220 may be formed of relatively inextendable material which breaks at tensions just above the tension in which the pre-determined degree of stretching of the fabric is attained (e.g. thin cotton thread). Alternatively it may be an elastic material which is capable of a limited degree of further extension and which thus indicates a range of extensions of the bandage.

Figure 6:
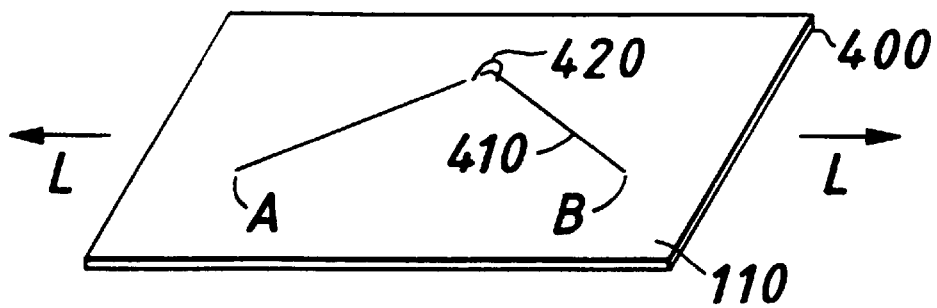
FIG. 6 shows a plan view of a further alternative bandage according to the present invention in inextended form.
Figure 6:

Referring now to FIG. 6, a further indicator is shown which is a cotton thread 410, releasably held by loop 420. Stretching of substrate 110 to a pre-determined degree causes loop 420 to break so as to release thread 410, thereby causing a distinctive change in configuration of the thread 110.

At a given further degree of stretching of fabric 110, thread 410 forms a straight line between points A and B, thereby causing a further distinctive change in configuration.

The above mentioned two changes in configuration can be correlated with two pre-determined degrees of extensions of fabric by using an appropriate length of thread 410 with a suitably positioned loop 420 of an apt breaking strain. Thus a user of the bandage 400 can determine when it is within a given range of extension.

What is claimed is:

1. An extensible article comprising an extensible fabric and an extension indicator, wherein said extension indicator comprises a flexible elongate member, the ends of said elongate member being interlaced at points on a surface of said fabric, said points locating a line defining direction of extension of the fabric, the length of said elongate member being greater than the distance between said points when said fabric is in its unextended state, said elongate member forming a loop having a configuration distinct from said surface of the fabric and separable from said surface of the fabric when the fabric is in its unextended state.

2. An extensible article according to claim 1 wherein said extensible fabric is elastic.

3. An extensible article according to claim 1 wherein said extensible fabric is woven.

4. An extensible article according to claim 1 wherein said extensible fabric comprises elastic fibers.

5. An extensible article according to claim 1 wherein said flexible elongate member has a length at least ten times its width.

6. An extensible article according to claim 1 wherein said indicator comprises a plurality of said loops.

7. An extensible article according to claim 6 wherein said loops adopt a configuration on extension of the fabric to a pre-determined extent which is visually distinct from the configuration adopted when extension of the fabric is below the pre-determined extent.

8. An extensible article according to claim 6 wherein said loops are provided with further extension indicator means.

9. An extensible article according to claim 8 wherein said further extension indicator is substantially continuous in the direction of extension.

10. An extensible article according to claim 1 comprising at least two of said extension indicators to indicate at least two pre-determined degrees of extension of the fabric.

11. An extensible article according to claim 1, which article is a bandage.

12. A method of treatment of one or more of the following disorders; namely, venous disorders, lymphoedema, which comprises applying an article according to claim 1 to an affected site on a patient.

13. A method of providing an extension indicator on a surface of an extensible fabric comprising:

(a) providing an extensible fabric; and (b) interlacing the ends of a flexible elongate member at points on said surface of said fabric, said points locating a line defining a direction of extension of the fabric, the length of said elongate member being greater than the distance between said points when said fabric is in its unextended state, said elongate member forming a loop having a configuration distinct from said surface of the fabric and separable from said surface of the fabric when the fabric is in its unextended state.

14. A method according to claim 13 comprising weaving said fabric under tension and altering the frequency of weft insertion at predetermined points, whereby said elongate member is interlaced as part of the weaving process.

15. A method according to claim 13 comprising preparing said fabric under tension and interlacing the elongate member by stitching to provide a plurality of said indicator loops.

16. A method according to claim 15 wherein said loops alternate on both sides of the fabric.

17. A method according to claim 15 comprising interlacing a further extension indicator through said loops.

* * * * *